United States Patent [19]
Mayeux

[11] Patent Number: 5,311,865
[45] Date of Patent: May 17, 1994

[54] PLASTIC FINGER OXIMETRY PROBE HOLDER

[76] Inventor: Charles D. Mayeux, 825 Roseland Pky., Harahan, La. 70123

[21] Appl. No.: 788,840

[22] Filed: Nov. 7, 1991

[51] Int. Cl.⁵ .................................................. A61B 5/00
[52] U.S. Cl. .................................... 128/633; 128/632; 128/637; 128/691
[58] Field of Search ............... 128/632, 633, 637, 639, 128/678, 691, 880, 395; 602/2, 22

[56] References Cited

U.S. PATENT DOCUMENTS

| | | | |
|---|---|---|---|
| 3,152,587 | 10/1964 | Ullrich et al. | 128/633 |
| 3,229,685 | 1/1966 | Ringkamp et al. | 128/667 |
| 3,482,565 | 12/1969 | Gowen | 128/667 |
| 4,539,997 | 9/1985 | Wesseling et al. | 128/667 |
| 4,564,355 | 1/1986 | Traiger et al. | 128/633 |
| 4,776,339 | 10/1988 | Schreiber | 128/633 |
| 4,825,872 | 5/1989 | Tan et al. | 128/633 |
| 4,825,879 | 5/1989 | Tan et al. | 128/633 |
| 4,834,532 | 5/1989 | Yount | 356/41 |
| 4,865,038 | 9/1989 | Rich et al. | 128/633 |
| 4,883,353 | 11/1989 | Hausman et al. | 356/41 |
| 4,927,264 | 5/1990 | Shiga et al. | 356/41 |
| 4,928,691 | 5/1990 | Nicolson et al. | 128/633 |
| 5,035,243 | 7/1991 | Muz | 128/633 |
| 5,069,213 | 12/1991 | Polczynski | 128/633 |
| 5,090,410 | 2/1992 | Saper et al. | 128/633 |
| 5,217,012 | 6/1993 | Young et al. | 128/633 |

Primary Examiner—Randall L. Green
Assistant Examiner—P. Zuttarelli
Attorney, Agent, or Firm—Pravel, Hewitt, Kimball & Krieger

[57] ABSTRACT

A holder, for a pulse oximetry probe having an infrared light transmitter and an infra-red light receiver, includes a pair of grippers for attaching the holder to a finger, a surface onto which a pulse oximetry probe may be attached, and a pair of visual apertures for allowing infra-red light from the transmitter of the pulse oximetry probe to travel through the holder to the receiver of the pulse oximetry probe.

9 Claims, 2 Drawing Sheets

PLASTIC FINGER OXIMETRY PROBE HOLDER

BACKGROUND OF THE INVENTION

1. Field of the Invention

The present invention relates to finger oximetry probes. More particularly, the present invention relates to a holder for finger oximetry probes.

2. General Background of the Invention

Pulse oximetry probes (pulse oximeters) are used to measure saturated oxygen (SaO2) by transmitting infrared light through a person's fingertip. Pulse oximeters are described, for example, in U.S. Pat. Nos. 4,825,872; 4,825,879; 4,865,038; 4,834,532; 4,883,353; and 4,927,264, all incorporated herein by reference.

Many manufacturers of pulse oximeters make disposable finger probes which are intended to be single-patient-use items. These probes typically cost around $15 each. The probes are made to be taped to one finger of the patient, but sometimes the probe needs to be moved from the first finger to another for improved pulse sensing. This movement from the first finger to another presently requires untaping and retaping the disposable probe, which can cause damage to the probe and its ability to adhere.

SUMMARY OF THE INVENTION

The apparatus of the present invention solves the problems confronted in the art in a simple and straightforward manner. What is provided is a holder to which the pulse oximetry probe is taped. The holder is either before or after taping placed on a patient's finger. If the probe needs to be moved to another of the patient's fingers, the holder is simply slipped off of the first finger and placed onto the other finger. The holder, with the probe attached, can be moved from finger to finger until proper pulse sensing is achieved.

The probe holder includes means for gripping a finger and a surface to which a pulse oximetry probe can be attached. It is necessary to ensure that the holder does not block transmission of light between the infrared transducers of the probe. In the preferred embodiment, this is accomplished by providing holes in the probe holder adjacent the infra-red transducers. If the probe holder is made of opaque material, this can be accomplished either by providing holes in the probe holder adjacent the infra-red transducers, or by providing an area of transparent plastic adjacent the infra-red transducers. Preferably, however, holes are provided, as holes allow good contact of the electronics in the pulse oximetry probe with the finger.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

PARTS LIST

Figure 1:
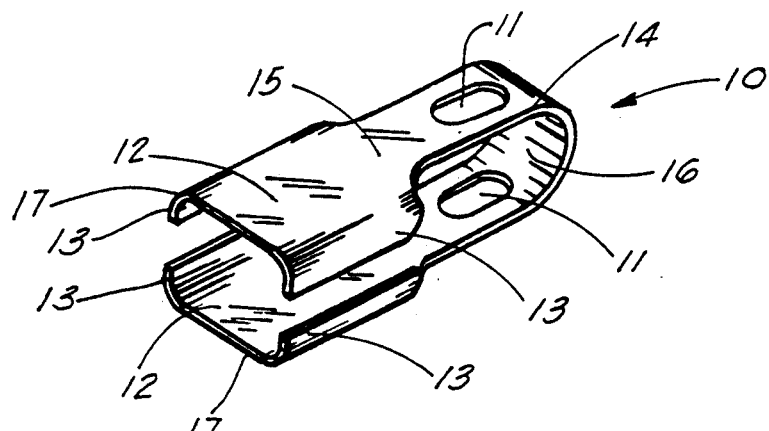
FIG. 1 is an overall view of a first embodiment of the apparatus of the present invention.
Figure 2:
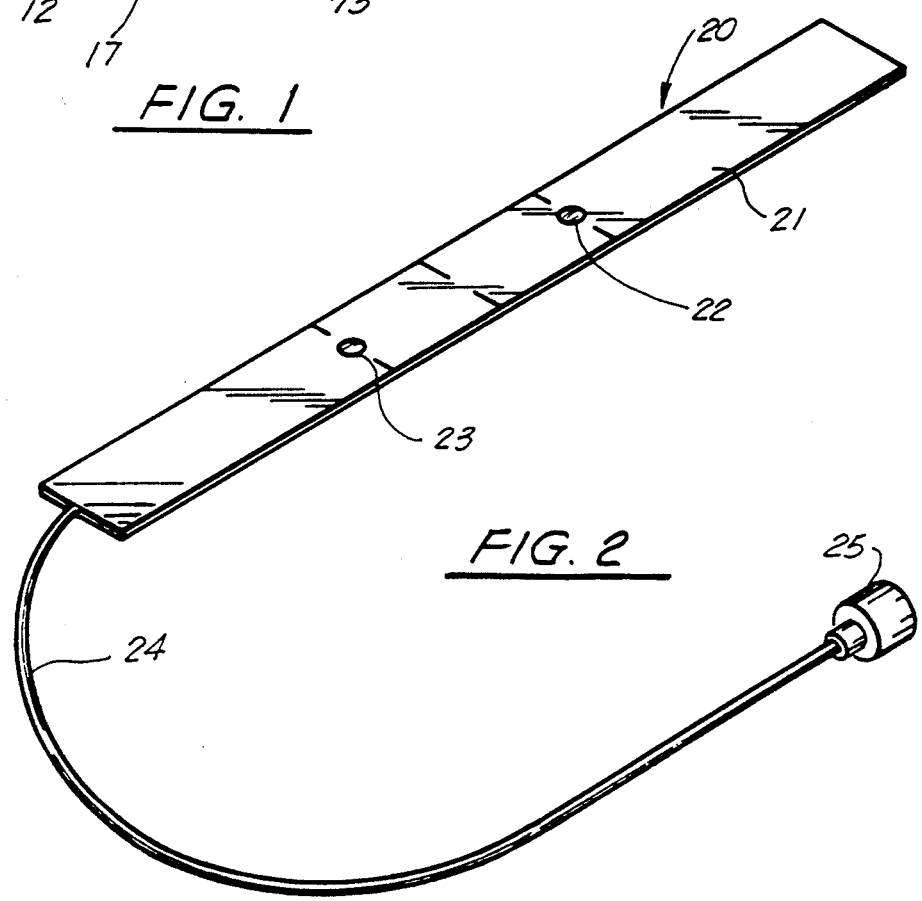
FIG. 2 is a view of a typical pulse oximeter with which the present invention is designed to be use.
Figure 3:
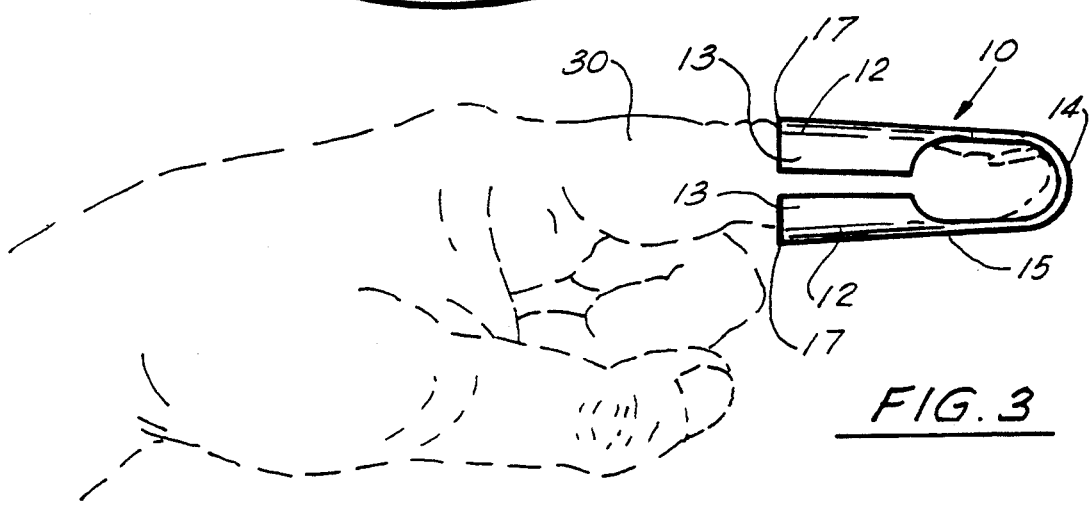
FIG. 3 shows the first embodiment of the present invention in position on a person's finger.

The following is a list of suitable parts and materials for the various elements of the present invention.

10 Pulse oximetry probe holder of the first embodiment of the present invention
11 Hole in probe holders 10 and 110
12 Finger grippers of holders 10, 110, and 210
13 Inwardly projecting arcuate portion of finger grippers 12
14 Finger-tip portion of probe-holder 10
15 Outer surface of pulse oximetry probe holder 10
16 Inner surface of pulse oximetry probe holder 10
17 Free ends of finger grippers 12
20 Nellcor ® brand pulse oximetry probe
21 Tape-covered surface of pulse oximetry probe 20
22 Infra-red transmitter of pulse oximetry probe 20
23 Infra-red receiver of pulse oximetry probe 20
24 Transmission wire of pulse oximetry probe 20
25 Coupling receptacle of pulse oximetry probe 20
110 Pulse oximetry probe holder of the preferred embodiment of the present invention
114 Finger-tip portion of probe-holder 110
115 Outer surface of pulse oximetry probe holder 110
116 Inner surface of pulse oximetry probe holder 110
210 Pulse oximetry probe holder of the third embodiment of the present invention
215 Outer surface of pulse oximetry probe holder 210
216 Inner surface of pulse oximetry probe holder 210

DETAILED DESCRIPTION OF THE PREFERRED EMBODIMENT

Figure 4:
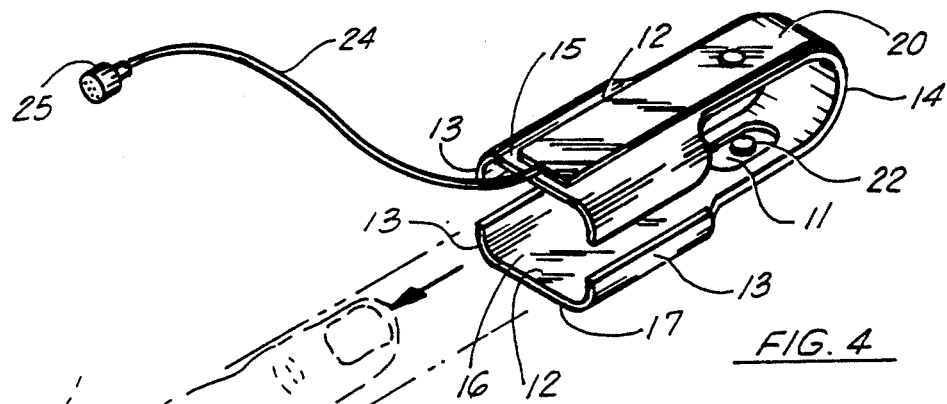
FIG. 4 shows the first embodiment of the present invention with the pulse oximeter of FIG. 2 mounted thereon.
Figure 6:
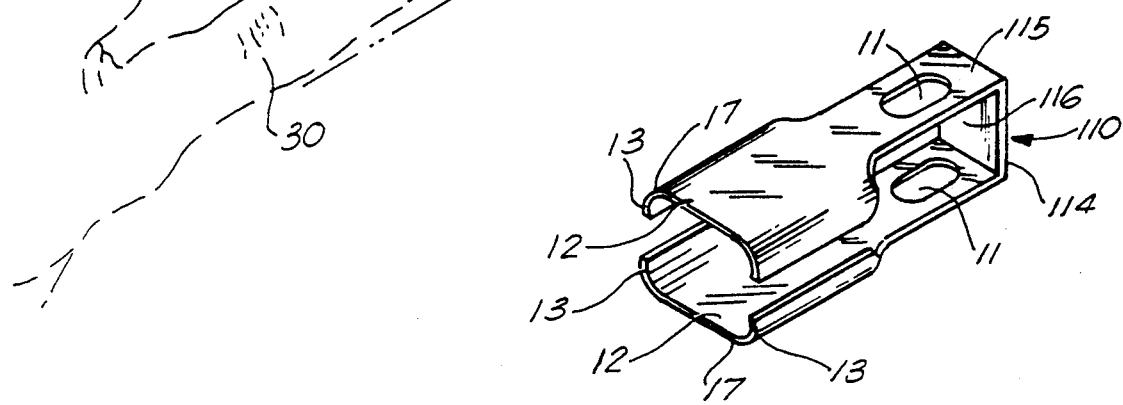
FIG. 6 is a perspective view of the preferred embodiment of the apparatus of the present invention.
Figure 5:
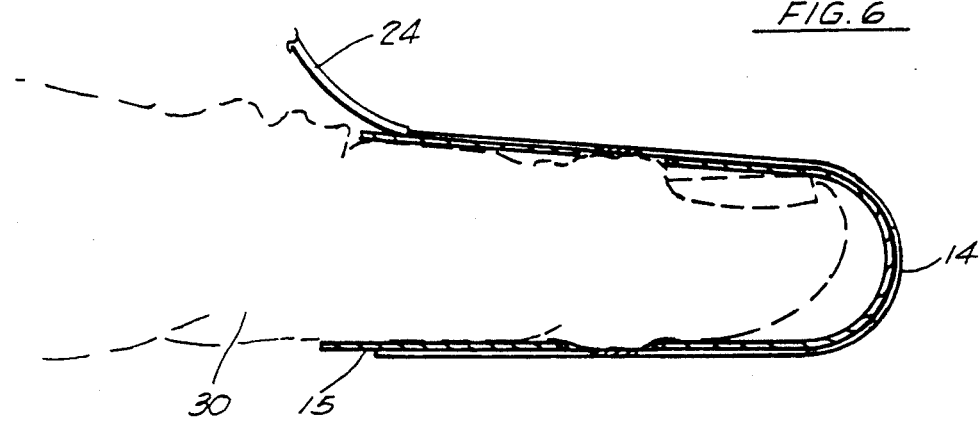
FIG. 5 is a cutaway view showing the set-up of FIG. 4.
Figure 7:
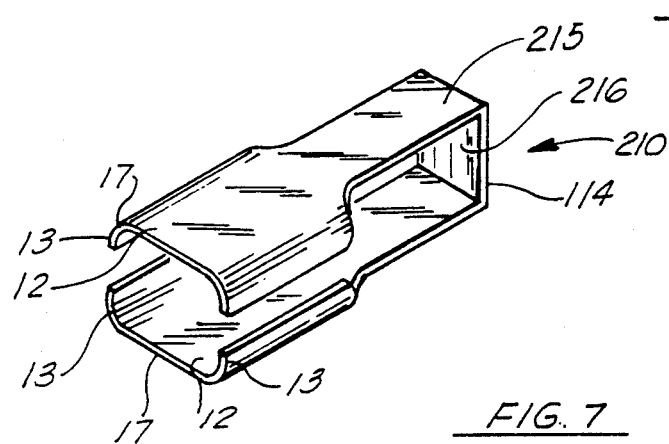
FIG. 7 is a perspective view of a third embodiment of the apparatus of the present invention.

FIGS. 1 and 3 through 5 show the first embodiment of the present invention, pulse oximetry probe holder 10. Pulse oximetry probe holder 10 includes two finger grippers 12 and an arcuate finger-tip portion 14. Finger grippers 12 each include two inwardly projecting arcuate portions 13. As shown in FIG. 4, a finger 30 is received in holder 10, adjacent inner surface 16 of pulse oximetry probe holder 10. On outer surface 15 of pulse oximetry probe holder 10 is disposed a pulse oximetry probe 20. Probe 20 includes a tape-covered surface 21, an infra-red transmitter 22, an infra-red receiver 23, a transmission wire 24, and a coupling receptacle 25.

There are two elongated holes 11 in probe holder 10 which act as visual aperture means for allowing infrared light to be transmitted by infra-red transmitter 22 to infra-red receiver 23 through holder 10 and finger 30.

Holder 10 is placed on a patient's finger 30 either before or after taping pulse oximetry probe 20 on the outer surface 15 thereof. If probe 10 needs to be moved to another of the patient's fingers, holder 10 is simply slipped off of the first finger and placed onto the other finger. Holder 10, with probe 20 attached, can be moved from finger to finger until proper pulse sensing is achieved.

Holder 10 is shaped so that it acts as a leaf spring, with finger grippers 12 spreading apart when finger 30 is inserted therein. Holder 10 can be made in various sizes to fit various sizes of fingers 30. Ideally, the distance between the free ends 17 of finger grippers 12 is smaller than the height of the finger 30 which it is designed to fit, so that the spring action of holder 10 will hold holder 10 on finger 30 (this does not necessarily mean that the distance between the other ends of finger grippers 12 needs to be less than the height of the finger 30 which it is designed to fit). Thus, finger grippers 12 act as attachment means for holding holder 10 on a finger 30.

Pulse oximetry probe holder 110, the preferred embodiment of the present invention, is similar to holder 110, the only difference being that the finger-tip portion 114 of probe-holder 110 is squared off instead of being arcuate. A finger 30 can be received in holder 110, adjacent inner surface 116 of pulse oximetry probe holder 110. Outer surface 115 of pulse oximetry probe holder 110 can receive pulse oximetry probe 20.

The height of vertical finger-tip portion 114 of holder 110 is preferably greater than the distance between the free ends 17 of finger grippers 12 so that holder 110 will snugly fit on a finger 30 even if the height of the finger is substantially equal to the height of vertical portion 114.

Pulse oximetry probe holder 210 of the third embodiment of the present invention includes an outer surface 215 for receiving pulse oximetry probe 20 and an inner surface 216 for receiving a finger 30. It differs from probe holder 110 in that it does not include holes 111. Because pulse oximetry probe holder 210 does not include holes 11, it must either be made of transparent material or at least have transparent material in the area of holder 210 corresponding roughly to holes 11.

Preferably all of the parts of the present invention are made of transparent plastic (such as Lexan ® brand sheet plastic). If opaque material is used instead, some visual aperture means must be present in the holder to allow unimpeded transmission of infra-red light from the infrared transmitter 22 to the infra-red receiver 23. The visual aperture means may comprise holes 11 in holders 10 and 110. In holder 210, the visual aperture means comprises transparent plastic at at least the portions of holder 210 adjacent infra-red transducers 22 and 23 (preferably, the transparent plastic occupies an area adjacent each transducer 22, 23 from the outer surface 215 to the inner surface 216 approximately equal to the area of holes 11).

Even when transparent plastic is used to make holders 10 and 110, it is still advantageous to provide holes 11, as holes 11 allow transmitter 22 and receiver 23 to physically as well as optically contact finger 30. This eliminates any chance that holders 10 or could interfere with the proper operation of pulse oximetry probe 20.

Holes 11 are elongated slots to allow lateral adjustment of the infra-red receiver 2 and infra-red transmitter 22 relative to a finger 30 without moving holders 10 or 110 relative to finger 30, even when holders 10 and 110 are made of opaque material.

As used herein, "opaque material" refers to material which does not allow unimpeded transmission of infrared light.

As can be seen in the drawings, holder 10 is U-shaped. As one can appreciate from the description of holder 10 acting as a leaf spring and gripping a finger, it is made of a resilient material, and finger grippers 12 are each biased towards the other finger gripper. As can be seen in the drawings, the inwardly projecting arcuate portions 13 of finger grippers 12 conform to the contour of a user's finger.

The foregoing embodiments are presented by way of example only; the scope of the present invention is to be limited only by the following claims.

I claim:

1. Apparatus including a pulse oximetry probe and a holder for placement between the pulse oximetry probe and a finger, the pulse oximetry probe having a light transmitter and a light receive, the holder comprising:
   (a) attachment means for attaching the holder to the finger;
   (b) an outer surface onto which the pulse oximetry probe is removably attached so that the probe may be moved from one finger to another;
   (c) visual aperture means in the holder for allowing light from the light transmitter of the pulse oximetry probe to travel completely through the holder from the outer surface of the holder to the light receiver of the pulse oximetry probe when the pulse oximetry probe is attached to the outer surface of the holder.

2. The apparatus of claim 1, wherein:
   the visual aperture means comprises two holes in the holder, a first hole adjacent the light transmitter of the pulse oximetry probe and a second hole adjacent the light receiver of the pulse oximetry probe.

3. The apparatus of claim 2, wherein:
   the hole are elongated slots to allow lateral adjustment of the light receiver and light transmitter relative to a finger without moving the holder relative to the finger.

4. The apparatus of claim 1, wherein:
   the visual aperture means comprises clear plastic, which clear plastic is used to construct at least a portion of the holder adjacent the light transmitter of the pulse oximetry probe and at least a portion of the holder adjacent the light receiver of the pulse oximetry probe.

5. The apparatus of claim 1, wherein:
   the attachment means comprise two finger grippers, each finger gripper including two inwardly projecting arcuate portions,
   the holder is shaped so that it acts as a leaf spring, with the finger grippers spreading apart when the finger is inserted therein,
   the finger grippers each have a first end connected to a finger-tip portion of the holder and a second, free end, and
   the distance between the free ends of the finger grippers is smaller than the height of the finger which it is designed to fit, so that spring action of the holder will hold the holder on the finger.

6. A U-shaped pulse oximetry probe holder made of a resilient material, the holder including:
   (a) two finger grippers, each finger gripper being biased towards the other finger gripper and including two inwardly projecting arcuate portions that conform to the contour of a user's finger;
   (b) a finger-tip portion;
   (c) an inner surface for receiving the user's finger;
   (d) an outer surface for receiving a pulse oximetry probe having a tape-covered surface, an infra-red transmitter, and an infra-red receiver;
   (e) two elongated apertures extending all the way through the holder for allowing infra-red light to be transmitted by the infra-red transmitter to the infra-red receiver completely through the holder and the finger from the outer surface when the pulse oximetry probe is attached to the outer surface of the holder, wherein the holder is shaped so that it acts as a leaf spring, with the finger grippers spreading apart and gripping the finger when the finger is inserted therein, the finger grippers each having a first end connected to the finger-tip portion and a second, free end, and the distance between the free ends of the finger grippers is smaller than the height of the finger which it is designed to fit, so that spring action of the holder will hold the holder on the finger.

7. The holder of claim 6, wherein:
the height of the vertical finger-tip portion of the holder is preferably greater than the distance between the free ends of the finger grippers so that the holder will snugly fit on a finger even if the height of the finger is substantially equal to the height of the vertical finger-tip portion.

8. The holder of claim 6, wherein:
the holder is made of transparent plastic.

9. The holder of claim 6, wherein:
the apertures are shaped to allow lateral adjustment of the infra-red receiver and the infra-red transmitter receiver to a finger without moving the holder relative to the finger, even when the holder is made of a material which does not allow unimpeded transmission of infra-red light.

* * * * *